(12) United States Patent
Nagata et al.

(10) Patent No.: US 6,951,919 B1
(45) Date of Patent: Oct. 4, 2005

(54) FAS LIGAND DERIVATIVE

(75) Inventors: Shigekazu Nagata, Minoo (JP); Masato Tanaka, Minoo (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/508,849

(22) PCT Filed: Sep. 17, 1998

(86) PCT No.: PCT/JP98/04187

§ 371 (c)(1),
(2), (4) Date: Mar. 17, 2000

(87) PCT Pub. No.: WO99/14325

PCT Pub. Date: Mar. 25, 1999

(30) Foreign Application Priority Data

Sep. 17, 1997 (JP) ............................................. 9-252541

(51) Int. Cl.$^7$ .......................... C07K 1/00; C07K 14/00; C07K 17/00; C07K 2/00; A61K 38/00
(52) U.S. Cl. ........................... 530/350; 530/300; 536/1; 536/18.7; 536/22.1; 536/23.1; 536/23.4; 536/23.5; 435/7.6
(58) Field of Search .............................. 530/300, 350; 536/1, 18.7, 22.1, 23.1, 23.4, 23.5; 435/7.6

(56) References Cited

U.S. PATENT DOCUMENTS 6,183,951 B1 * 2/2001 Plevy et al.
2002/0064869 A1 * 5/2002 Ebner
2002/0081647 A1 * 6/2002 Ebner

FOREIGN PATENT DOCUMENTS

| JP | 9-124510 A | 5/1997 |
| WO | WO9821232 | 5/1998 |

OTHER PUBLICATIONS

Hurtenbach et al. Prevention of Autoimmune Diabetes in Non–Obese Diabetic Mice by Treatment with a Class II Major Histocompatibility Complex–blocking Peptide. J. Exp. Med 177:1499–1504, May 1993.*
Amino acid database, Accession A49266, Jan. 13, 1995.*
Suda et al. Molecular cloning and expression of the Fas ligand, a novel member of the tumor necrosis factor family. Cell 75:1169–1178, Dec. 17, 1993.*
Amino acid and nucleic acid database sheets, Sequences 11, 13 and 14 of U.S. Patent No. 6,183,951.*
GenCore database sheets. Amino acid comparison between Applicants' Seq Id No.: 17 and prior art, 3 sheets.*
Takahashi et al. Human Fas ligand: gene structure, chromosomal location and species specificity. International Immunology 6(10): 1567–1574, 1994.*
Mita et al. Role of Fas ligand in apoptosis induced by hepatitis C virus infection. Biochemical and Biophysical Research Communications 204(2): 468–474, Oct. 28, 1994.*
Su et al. Cloning and characterization of gene TNF alpha encoding equine tumor necrosis factor alpha. Gene 107:319–321, 1991.*
Weil and Dautry. Induction of Tumor NEcrosis Factore alpha and beta and Interferon gamma mRNA by Interleukin 2 in Murine lymphocytic cell lines. Oncogene Research 3: 409–414, 1988.*
Gardner et al. Mouse lymphotoxin and tumor necrosis factor: structural analysis of the cloned genes, physical linkage and chromosomal position. The Journal of Immunology 139(2): 476–483, Jul. 15, 1987.*
Gray et al. Cloning and expression of cDNA for human lymphotoxin, a lymphokine with tomour necrosis activity. Nature 312 (20/27): 721–724, Dec. 1984.*
Tanaka, M. et al., Nature Medicine (1996) vol. 2, No. 3 p. 317–322.
Takahashi, T. et al., International Immunology (1994) vol. 6, No. 10 p–1567–1575.
Tanaka, M. et al., Nature Medicine (1998) vol. 4, No. 5 p–31–36.

* cited by examiner

*Primary Examiner*—Alana M. Harris
(74) *Attorney, Agent, or Firm*—Birch, Stewart, Kolasch & Birch, LLP

(57) ABSTRACT

This invention provides a soluble Fas ligand which functions as a Fas antagonist or an apoptosis regulator, a novel Fas ligand derivative which has excellent apoptosis-inducing activity and cytotoxic activity, and a DNA encoding such peptide.

9 Claims, 7 Drawing Sheets

SEQUENCE LISTING

```
<160> NUMBER OF SEQ ID NOS: 17

<210> SEQ ID NO 1
<211> LENGTH: 258
<212> TYPE: PRT
<213> ORGANISM: Artificial Sequence
<220> FEATURE:
<223> OTHER INFORMATION: Description of Artificial Sequence:amino acids
      at 111-133 from N terminal are deleted from natural human
      Fas ligand

<400> SEQUENCE: 1

Met Gln Gln Pro Phe Asn Tyr Pro Tyr Pro Gln Ile Tyr Trp Val Asp
  1               5                  10                  15

Ser Ser Ala Ser Ser Pro Trp Ala Pro Pro Gly Thr Val Leu Pro Cys
             20                  25                  30

Pro Thr Ser Val Pro Arg Arg Pro Gly Gln Arg Arg Pro Pro Pro Pro
         35                  40                  45

Pro Pro Pro Pro Pro Leu Pro Pro Pro Pro Pro Pro Pro Pro Leu Pro
     50                  55                  60

Pro Leu Pro Leu Pro Pro Leu Lys Lys Arg Gly Asn His Ser Thr Gly
 65                  70                  75                  80

Leu Cys Leu Leu Val Met Phe Phe Met Val Leu Val Ala Leu Val Gly
                 85                  90                  95

Leu Gly Leu Gly Met Phe Gln Leu Phe His Leu Gln Lys Glu Pro Ser
            100                 105                 110

Pro Pro Pro Glu Lys Lys Glu Leu Arg Lys Val Ala His Leu Thr Gly
        115                 120                 125

Lys Ser Asn Ser Arg Ser Met Pro Leu Glu Trp Glu Asp Thr Tyr Gly
    130                 135                 140

Ile Val Leu Leu Ser Gly Val Lys Tyr Lys Lys Gly Gly Leu Val Ile
145                 150                 155                 160

Asn Glu Thr Gly Leu Tyr Phe Val Tyr Ser Lys Val Tyr Phe Arg Gly
                165                 170                 175
```

-continued

Gln Ser Cys Asn Asn Leu Pro Leu Ser His Lys Val Tyr Met Arg Asn
            180                 185                 190

Ser Lys Tyr Pro Gln Asp Leu Val Met Met Glu Gly Lys Met Met Ser
        195                 200                 205

Tyr Cys Thr Thr Gly Gln Met Trp Ala Arg Ser Ser Tyr Leu Gly Ala
    210                 215                 220

Val Phe Asn Leu Thr Ser Ala Asp His Leu Tyr Val Asn Val Ser Glu
225                 230                 235                 240

Leu Ser Leu Val Asn Phe Glu Glu Ser Gln Thr Phe Phe Gly Leu Tyr
                245                 250                 255

Lys Leu

<210> SEQ ID NO 2
<211> LENGTH: 277
<212> TYPE: PRT
<213> ORGANISM: Artificial Sequence
<220> FEATURE:
<223> OTHER INFORMATION: Description of Artificial Sequence:amino acids
      at 128-131 from N terminal are deleted from natural human
      Fas ligang

<400> SEQUENCE: 2

Met Gln Gln Pro Phe Asn Tyr Pro Tyr Pro Gln Ile Tyr Trp Val Asp
 1               5                  10                  15

Ser Ser Ala Ser Ser Pro Trp Ala Pro Pro Gly Thr Val Leu Pro Cys
                20                  25                  30

Pro Thr Ser Val Pro Arg Arg Pro Gly Gln Arg Arg Pro Pro Pro Pro
            35                  40                  45

Pro Pro Pro Pro Pro Leu Pro Pro Pro Pro Pro Pro Pro Pro Leu Pro
        50                  55                  60

Pro Leu Pro Leu Pro Pro Leu Lys Lys Arg Gly Asn His Ser Thr Gly
65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Gly
        115                 120                 125

His Pro Ser Pro Pro Glu Lys Lys Glu Leu Arg Lys Val Ala His
    130                 135                 140

Leu Thr Gly Lys Ser Asn Ser Arg Ser Met Pro Leu Glu Trp Glu Asp
145                 150                 155                 160

Thr Tyr Gly Ile Val Leu Leu Ser Gly Val Lys Tyr Lys Lys Gly Gly
                165                 170                 175

Leu Val Ile Asn Glu Thr Gly Leu Tyr Phe Val Tyr Ser Lys Val Tyr
            180                 185                 190

Phe Arg Gly Gln Ser Cys Asn Asn Leu Pro Leu Ser His Lys Val Tyr
        195                 200                 205

Met Arg Asn Ser Lys Tyr Pro Gln Asp Leu Val Met Met Glu Gly Lys
    210                 215                 220

Met Met Ser Tyr Cys Thr Thr Gly Gln Met Trp Ala Arg Ser Ser Tyr
225                 230                 235                 240

Leu Gly Ala Val Phe Asn Leu Thr Ser Ala Asp His Leu Tyr Val Asn
                245                 250                 255

Val Ser Glu Leu Ser Leu Val Asn Phe Glu Glu Ser Gln Thr Phe Phe
            260                 265                 270

```
Gly Leu Tyr Lys Leu
        275

<210> SEQ ID NO 3
<211> LENGTH: 281
<212> TYPE: PRT
<213> ORGANISM: Artificial Sequence
<220> FEATURE:
<223> OTHER INFORMATION: Description of Artificial Sequence:point
      mutation of a substitution of Lys 129 for Ala from N terminal is
      present in natural human Fas ligand <D6>

<400> SEQUENCE: 3

Met Gln Gln Pro Phe Asn Tyr Pro Tyr Pro Gln Ile Tyr Trp Val Asp
 1               5                  10                  15

Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Arg Pro Pro Pro Pro
        35                  40                  45

Pro Pro Pro Pro Pro Leu Pro Pro Pro Pro Pro Pro Pro Pro Leu Pro
    50                  55                  60

Pro Leu Pro Leu Pro Leu Lys Lys Arg Gly Asn His Ser Thr Gly
65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
        115                 120                 125

Ala Gln Ile Gly His Pro Ser Pro Pro Pro Glu Lys Lys Glu Leu Arg
    130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
        195                 200                 205

His Lys Val Tyr Met Arg Asn Ser Lys Tyr Pro Gln Asp Leu Val Met
    210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
            260                 265                 270

Gln Thr Phe Phe Gly Leu Tyr Lys Leu
        275                 280

<210> SEQ ID NO 4
<211> LENGTH: 774
<212> TYPE: DNA
<213> ORGANISM: Artificial Sequence
<220> FEATURE:
<223> OTHER INFORMATION: Description of Artificial Sequence:DNA coding
      for amino acids SEQ ID No.1
```

```
<400> SEQUENCE: 4
atgcagcagc ccttcaatta cccatatccc cagatctact gggtggacag cagtgccagc      60
tctccctggg cccctccagg cacagttctt ccctgtccaa cctctgtgcc cagaaggcct     120
ggtcaaagga ggccaccacc accaccgcca ccgccaccac taccacctcc gccgccgccg     180
ccaccactgc ctccactacc gctgccaccc tgaagaaga gagggaacca cagcacaggc     240
ctgtgtctcc ttgtgatgtt tttcatggtt ctggttgcct tggtaggatt gggcctgggg     300
atgtttcagc tcttccacct acagaaggag cccagtccac ccctgaaaa aaaggagctg     360 aggaaagtgg cccatttaac aggcaagtcc aactcaaggt ccatgcctct ggaatgggaa     420
gacacctatg gaattgtcct gctttctgga gtgaagtata agaagggtgg ccttgtgatc     480
aatgaaactg gctgtacttt gtatattcc aaagtatact tccggggtca atcttgcaac     540
aacctgcccc tgagccacaa ggtctacatg aggaactcta agtatcccca ggatctggtg     600
atgatggagg ggaagatgat gagctactgc actactgggc agatgtgggc ccgcagcagc     660
tacctggggg cagtgttcaa tcttaccagt gctgatcatt tatatgtcaa cgtatctgag     720
ctctctctgg tcaattttga ggaatctcag acgttttcg gcttatataa gctc           774

<210> SEQ ID NO 5
<211> LENGTH: 831
<212> TYPE: DNA
<213> ORGANISM: Artificial Sequence
<220> FEATURE:
<223> OTHER INFORMATION: Description of Artificial Sequence:DNA coding
      for amino acids SEQ ID No.2

<400> SEQUENCE: 5
atgcagcagc ccttcaatta cccatatccc cagatctact gggtggacag cagtgccagc      60
tctccctggg cccctccagg cacagttctt ccctgtccaa cctctgtgcc cagaaggcct     120
ggtcaaagga ggccaccacc accaccgcca ccgccaccac taccacctcc gccgccgccg     180
ccaccactgc ctccactacc gctgccaccc tgaagaaga gagggaacca cagcacaggc     240
ctgtgtctcc ttgtgatgtt tttcatggtt ctggttgcct tggtaggatt gggcctgggg     300
atgtttcagc tcttccacct acagaaggag ctggcagaac tccgagagtc taccagccag     360
atgcacacag catcatcttt gggccacccc agtccacccc ctgaaaaaaa ggagctgagg     420
aaagtggccc atttaacagg caagtccaac tcaaggtcca tgcctctgga atgggaagac     480
acctatggaa ttgtcctgct ttctggagtg aagtataaga agggtggcct tgtgatcaat     540 gaaactggc tgtactttgt atattccaaa gtatacttcc ggggtcaatc ttgcaacaac     600
ctgcccctga gccacaaggt ctacatgagg aactctaagt atccccagga tctggtgatg     660 atgggggga agatgatgag ctactgcact actgggcaga tgtgggcccg cagcagctac     720 ctggggggcag tgttcaatct taccagtgct gatcatttat atgtcaacgt atctgagctc     780
tctctggtca attttgagga atctcagacg ttttcggct tatataagct c              831

<210> SEQ ID NO 6
<211> LENGTH: 843
<212> TYPE: DNA
<213> ORGANISM: Artificial Sequence
<220> FEATURE:
<223> OTHER INFORMATION: Description of Artificial Sequence:DNA coding
      for amino acids SEQ ID No.3

<400> SEQUENCE: 6
atgcagcagc ccttcaatta cccatatccc cagatctact gggtggacag cagtgccagc      60
```

```
tctccctggg cccctccagg cacagttctt ccctgtccaa cctctgtgcc cagaaggcct    120
ggtcaaagga ggccaccacc accaccgcca ccgccaccac taccacctcc gccgccgccg    180
ccaccactgc ctccactacc gctgccaccc ctgaagaaga gagggaacca cagcacaggc    240
ctgtgtctcc ttgtgatgtt tttcatggtt ctggttgcct tggtaggatt gggcctgggg    300
atgtttcagc tcttccacct acagaaggag ctggcagaac tccgagagtc taccagccag    360
atgcacacag catcatcttt ggaggcacaa ataggccacc ccagtccacc ccctgaaaaa    420
aaggagctga ggaaagtggc ccatttaaca ggcaagtcca actcaaggtc catgcctctg    480
gaatgggaag acacctatgg aattgtcctg ctttctggag tgaagtataa aagggtggc    540 cttgtgatca atgaaactgg gctgtacttt gtatattcca agtatactt ccggggtcaa    600 tcttgcaaca acctgcccct gagccacaag gtctacatga ggaactctaa gtatccccag    660
gatctggtga tgatggaggg gaagatgatg agctactgca ctactgggca gatgtgggcc    720
cgcagcagct acctgggggc agtgttcaat cttaccagtg ctgatcattt atatgtcaac    780
gtatctgagc tctctctggt caattttgag gaatctcaga cgttttttcgg cttatataag    840 ctc                                                                  843
```

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:a sense
      primer BOS6

<400> SEQUENCE: 7

```
cctcagacag tggttcaaag                                                 20
```

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence:an antisense
      deletion primer DA4

<400> SEQUENCE: 8

```
ttttcagggg gtggactggg ctccttctgt aggtggaag                            39
```

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence:HFLP3

<400> SEQUENCE: 9

```
gctctagaac attctcggtg cctgtaac                                        28
```

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:DA5

<400> SEQUENCE: 10

```
tggactgggg tggcccaaag atgatgctgt                                      30
```

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence:DA6

<400> SEQUENCE: 11
ggggtggcct atttgtgcct ccaaagatga tgc                       33

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence:sequence of
      human FasL from amino acids 130 to137

<400> SEQUENCE: 12

Gln Ile Gly His Pro Ser Pro Pro
  1               5

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence:the amino
      acid sequence around the cleavage site of FasL

<400> SEQUENCE: 13

Glu Lys Gln Ile
  1

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence:the cleavage
      site of THN-alpha

<400> SEQUENCE: 14

Leu Ala Gln Ala Val Arg Ser Ser
  1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence:the cleavage
      site of CD40

<400> SEQUENCE: 15

Asn Ser Phe Glu Met Gln Lys Gly
  1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence:the cleavage
      site of FasL

<400> SEQUENCE: 16

```
Ser Leu Glu Lys Gln Ile Gly His
 1               5

<210> SEQ ID NO 17
<211> LENGTH: 281
<212> TYPE: PRT
<213> ORGANISM: Homo sapiens

<400> SEQUENCE: 17

Met Gln Gln Pro Phe Asn Tyr Pro Tyr Pro Gln Ile Tyr Trp Val Asp
 1               5                  10                  15

Ser Ser Ala Ser Ser Pro Trp Ala Pro Pro Gly Thr Val Leu Pro Cys
                20                  25                  30

Pro Thr Ser Val Pro Arg Arg Pro Gly Gln Arg Arg Pro Pro Pro Pro
                35                  40                  45

Pro Pro Pro Pro Pro Leu Pro Pro Pro Pro Pro Pro Pro Pro Leu Pro
        50                  55                  60

Pro Leu Pro Leu Pro Pro Leu Lys Lys Arg Gly Asn His Ser Thr Gly
65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
                100                 105                 110

Glu Leu Arg Glu Ser Thr Ser Gln Met His Thr Ala Ser Ser Leu Glu
            115                 120                 125

Lys Gln Ile Gly His Pro Ser Pro Pro Pro Glu Lys Lys Glu Leu Arg
        130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
                180                 185                 190

Ser Lys Val Tyr Phe Arg Gly Gln Ser Cys Asn Asn Leu Pro Leu Ser
                195                 200                 205

His Lys Val Tyr Met Arg Asn Ser Lys Tyr Pro Gln Asp Leu Val Met
        210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
                260                 265                 270

Gln Thr Phe Phe Gly Leu Tyr Lys Leu
            275                 280
```

FAS LIGAND DERIVATIVE

This application is the national phase under 35 U.S.C. § 371 of PCT International Application No. PCT/JP98/04187 which has an International filing date of Sep. 17, 1998, which designated the United States of America.

TECHNICAL FIELD

This invention relates to the Fas ligand which is capable of controlling apoptosis involved in various diseases.

TECHNICAL BACKGROUND

Fas ligand (hereinafter referred to as FasL) belongs to the tumor necrosis factor (TNF) family, which currently includes FasL, TNF, lymphotoxin, TRAIL (TNF related apoptosis-inducing ligand) CD40 ligand (CD40L), CD27 ligand (CD27L), CD30 ligand (CD30L), and OX40 ligand (OX40L) (Nagata, Cell, 88, 355–365, 1997; Willey et al., Immunity, 3, 673–682, 1995). Most members of the TNF family except for the α-chain of lymphotoxin are synthesized as type II-membrane proteins. However, soluble forms of FasL, TNF-α, and CD40L can be detected in the culture medium of the cell expressing these molecules, indicating that the TNF family members can be cleaved off from the membrane (cell surface) (Perez et al., Cell, 63, 251–258, 1990; Pietravalle et al., J. Biol. Chem., 271, 5965–5967, 1996b; Tanaka et al., EMBO J., 14, 1129–1135, 1995). Since metalloproteinase inhibitors prevent the shedding of FasL as well as TNF-α, it is thought that a metalloproteinase(s) is responsible for cleaving the membrane-bound FasL and TNF-α to their soluble form (Gearing et al., Nature 370, 555–557, 1994; McGeeham et al., Nature, 370, 558–561, 1994; Mohler et al., Nature, 370, 218–220, 1994; Tanaka et al., Nature Med. 2, 317–322, 1996). Recently, a metalloproteinase that specifically cleaves TNF-α has been identified as a member of the ADAM metalloproteinase family (Black et al., Nature 385, 729–733, 1997; Moss et al., Nature, 385, 733–736, 1997). However, the physiological roles of the shedding of TNF family members from the membrane have not been well characterized.

FasL induces apoptosis by binding to its receptor, Fas which is also called CD95 or APO-1 and which is a member of the TNF receptor family. FasL is predominantly expressed in activated T cells as in the case of natural killer (NK) cells (Arase et al., J. Exp. Med., 181, 1235–1238, 1995; Suda et al., J. Immunol., 154, 3806–3813, 1995; Tanaka et al., Nature Med. 2, 317–322, 1996), whereas Fas is ubiquitously expressed in various cells (French et al., J. Cell. Biol. 335–343, 1996; Leithauser et al., Lab. Invest. 69, 415–429, 1993; Suda et al., J. Immunol., 154, 3806–3813, 1995; Watanabe-Fukunaga et al., J. Immunol., 148, 1274–1279, 1992). Analyses of mice lacking Fas or FasL have indicated that FasL is one of the major effector molecules of cytotoxic T lymphocytes (CTLs), such as CD8-positive T cells and CD4-positive Th1-type T cells (Hanabuchi et al., Proc. Natl. Acad. Sci. USA, 91, 4930–4934, 1994; Suda et al., J. Immunol., 154, 3806–3813, 1995; Vignaux and Golstein, Eur. J. Immunol., 24, 923–927, 1994). The role of CTLs is to remove virally infected cells or cancer cells to prevent the spreading of viruses or cancer cells in animals. However, when this system overfunctions, it causes tissue destruction. The involvement of FasL-induced apoptosis in CTL-mediated autoimmune diseases such as hepatitis, insulin-dependent diabetes, and thyroiditis (Hashimoto's disease) has been demonstrated (Shervonsky et al., Cell 89, 17–24, 1997; Giordano et al., Science, 275, 960–963, 1997; Kondo et al., Nature Med., 3, 409–413, 1997).

As described above, membrane-bound FasL can be cleaved to become a soluble form. The human soluble FasL is functional in inducing apoptosis, at least in mouse WR19L cell transformants that overexpress Fas (Tanaka et al., EMBO J., 14, 1129–1135, 1995). Soluble FasL has been detected at a high level in the serum of human patients suffering from large granular leukemia of the T or NK-type, as well as NK lymphoma (Tanaka et al., Nature Med. 2, 317–322, 1996). Since the patients affected by these leukemias also often suffer from hepatitis and neutropenia, it has been postulated that the soluble FasL may cause systemic tissue damage, as found with TNF. However, when the human recombinant soluble FasL was injected into mice, a large amount of FasL was necessary to exihibit its lethal effect, even though the pretreatment of mice with Propionibacterium Acnes greatly sensitized them to the FasL-induced lethality (Tanaka et al., J. Immunol., 158, 2303–2309, 1997).

SUMMARY OF INVENTION

These results encouraged the inventors of the present invention to compare the cytotoxic activity of the soluble and the membrane-bound FasLs and to examine the physiological role of the shedding of FasL from membranes.

In this study, the inventors of the present invention purified human FasL from the culture medium of mouse T-cell transformants expressing human FasL. Its N-terminal amino acid sequence enabled the inventors to determine the cleavage site of human FasL. Deletion mutations around the FasL cleavage site completely prevented the cleavage of the membrane-bound form. Human Jurkat T cells and mouse hepatocytes were found to be resistant to soluble FasL, but they were effectively killed by membrane-bound FasL. Furthermore, soluble FasL worked as an inhibitor for the membrane-bound FasL-induced cytotoxicity for hepatocytes. These results suggest that the shedding of FasL from the membrane (cell surface) acts to downregulate the cytotoxic activity of FasL.

This invention provides soluble Fas ligand which functions as a Fas antagonist or an apoptosis regulator, a novel Fas ligand derivative having excellent apoptosis-inducing activity or cytotoxic activity, and a DNA coding for such peptide.

Fas ligand is a type II membrane protein which belongs to the tumor necrosis factor (TNF) family, and induces apoptosis by binding to Fas which is the receptor. FasL is cleaved by a putative processing enzyme, metalloproteinase to produce a soluble form. The inventors of the present invention purified human soluble FasL from the supernatant of the transformant mouse cell expressing human FasL, and identified the cleavage site. Deletion of 4 to 23 amino acids around the cleavage site blocked shedding of the human FasL from the membrane while the apoptosis-inducing activity was retained. Mouse WR19L cells overexpressing the Fas is sensitive to membrane-bound FasL as in the case with the FasL of soluble form whereas Jurkat cells and mouse primary hepatocytes which endogenously express a low level of Fas exhibited resistance to soluble FasL. When the membrane-bound FasL was used as an effector, the human Jurkat cells and the mouse hepatocytes were efficiently killed. Furthermore, soluble FasL inhibited cytotoxicity of the membrane-bound FasL to the mouse hepatocyte. These results indicate that the membrane-bound form of FasL is the functional form, and its activity is downregulated by the shedding of the soluble FasL from the membrane.

The present invention provides a Fas ligand derivative which has resistance, tolerance or reduced sensitivity to protease, and more specifically, a Fas ligand derivative having an amino acid sequence of natural human Fas ligand wherein amino acids 129–130 from N terminal are deleted or substituted, and at least one of amino acids 111–128 and 131–133 from N terminal is deleted or substituted, and a Fas ligand derivative having an amino acid sequence wherein amino acids 8–69 are further deleted. The present invention preferably provides a novel Fas ligand derivative having an amino acid sequence described in SEQ ID No. 1 or 2, and a DNA coding for such novel Fas ligand derivative.

Furthermore, the present invention provides a soluble Fas ligand which functions as a Fas antagonist or an apoptosis regulator; an apoptosis regulator containing such soluble Fas ligand; and a method wherein such soluble Fas ligand or apoptosis regulator is administered in order to prevent or treat a disease wherein Fas ligand-induced apoptosis is involved.

(A) shows the results of the analysis by SDS-polyacrylamide gel electrophoresis.

(B) is a graph showing the cytotoxic activity of soluble FasL.

Figure 2:
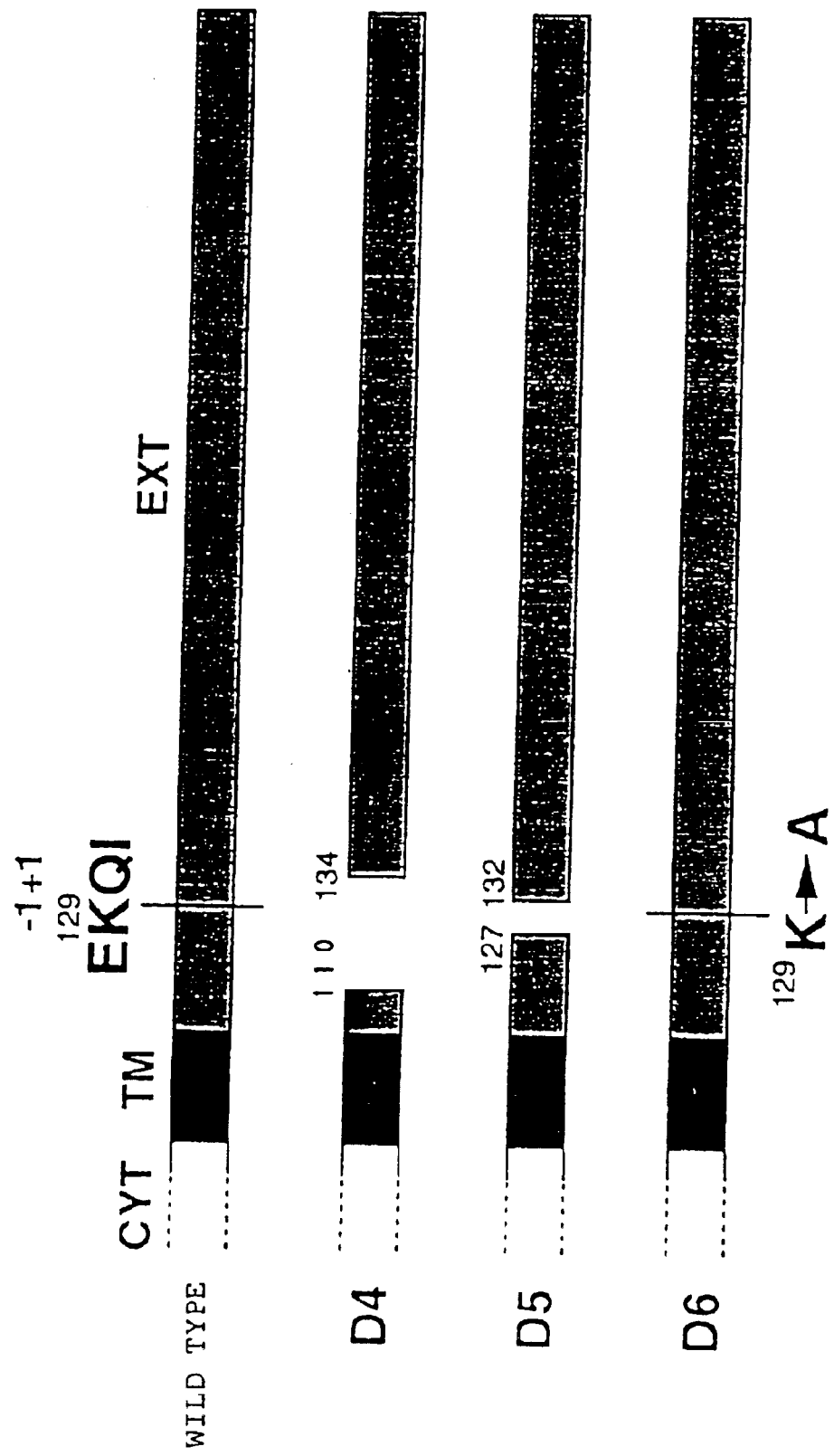

FIG. 2 is a schematic diagram of the FasL constructs carrying deletion or point mutation.

Figure 3:
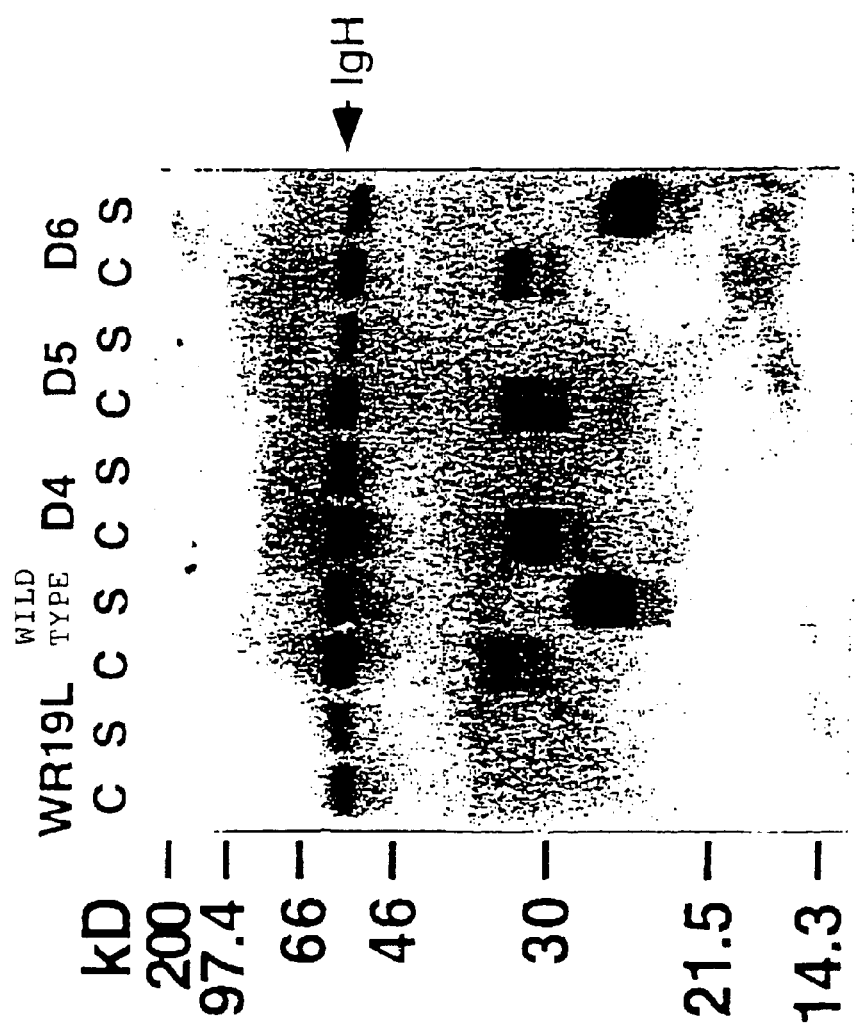

FIG. 3 shows the results of immunodetection of human FasL in the transformant cells.

Figure 4:
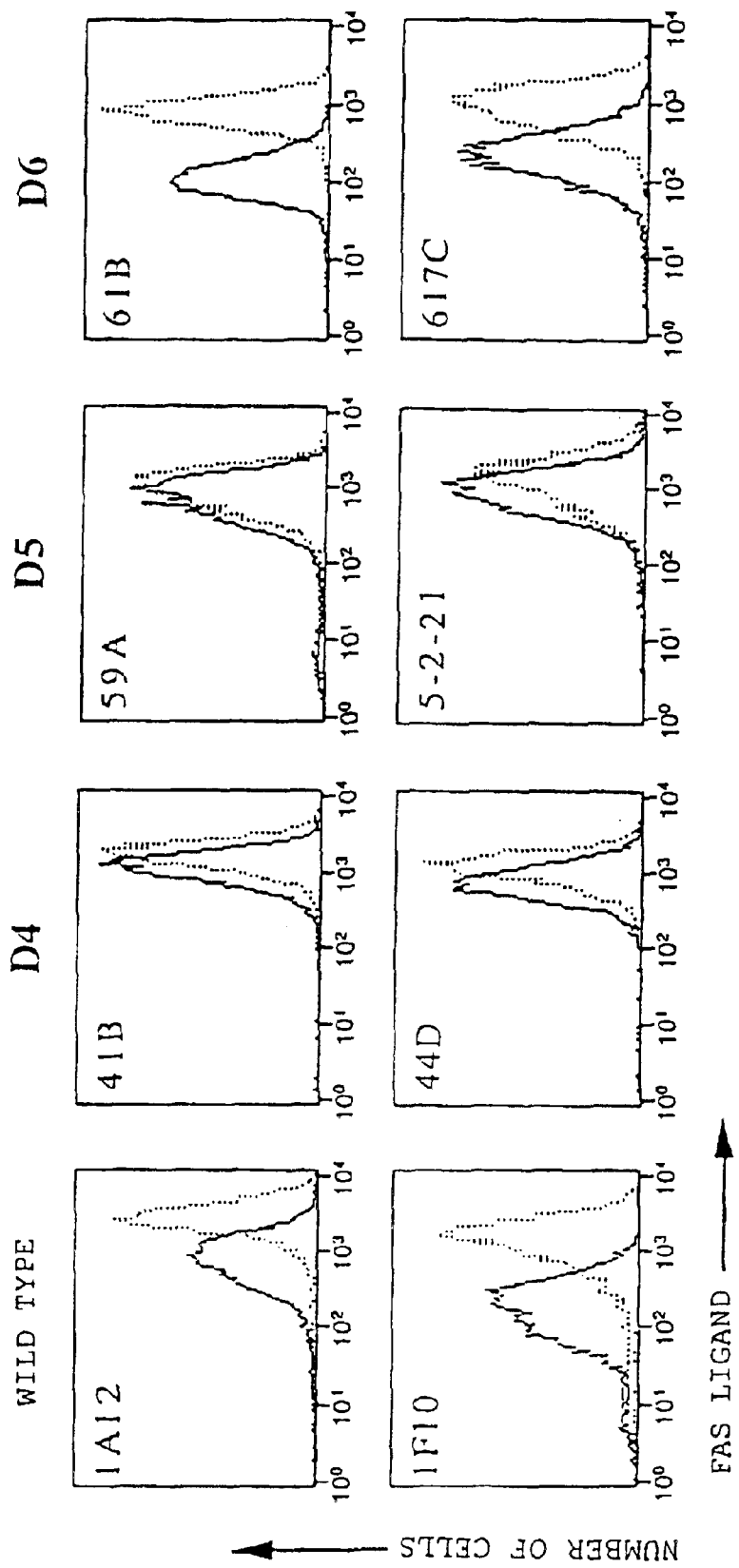

FIG. 4 shows the results of the expression of FasL on the cell surface.

Figure 5:
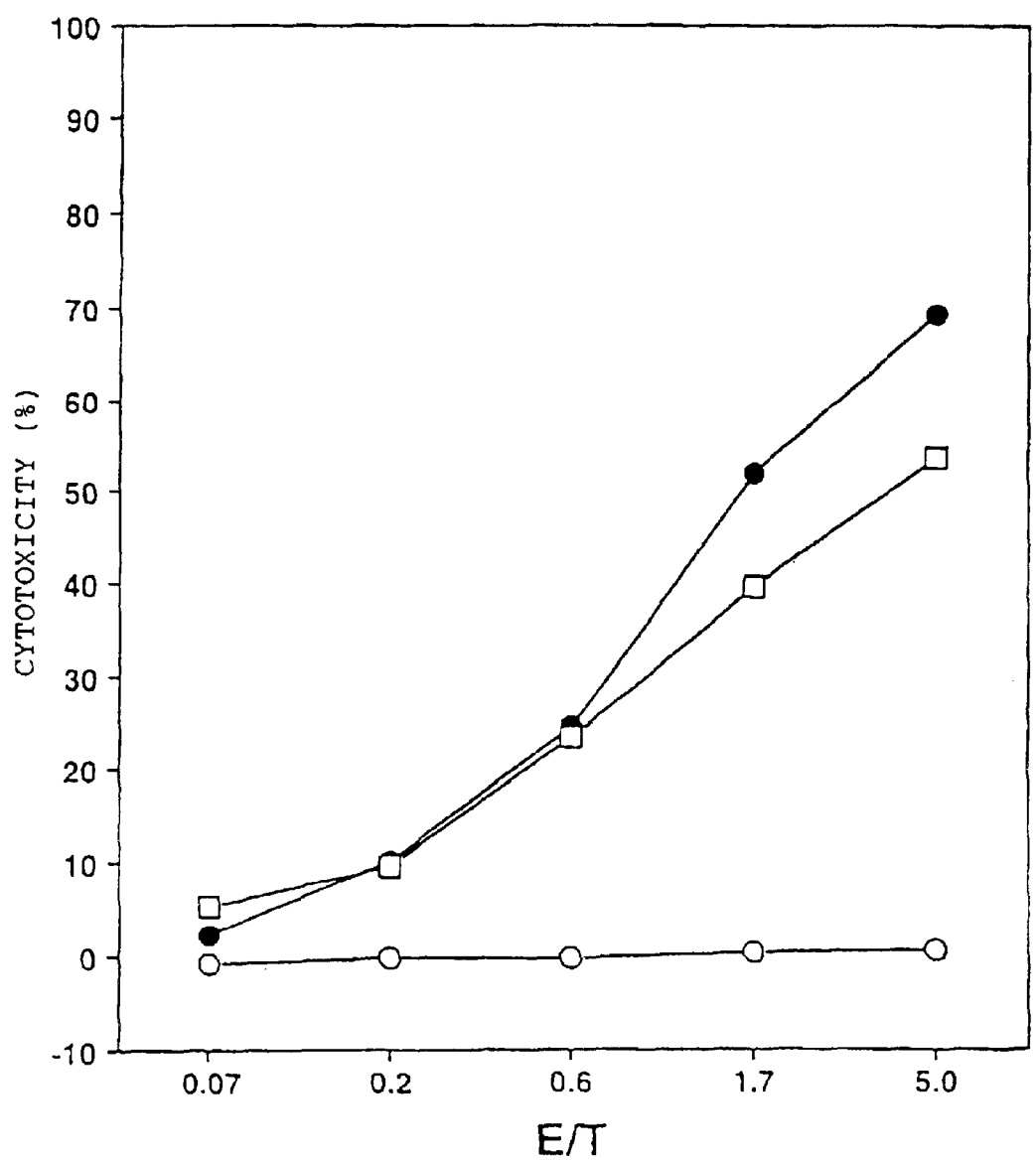

FIG. 5 shows the ability of the membrane-bound FasL to kill mouse W4 cells overexpressing Fas.

Figure 6:
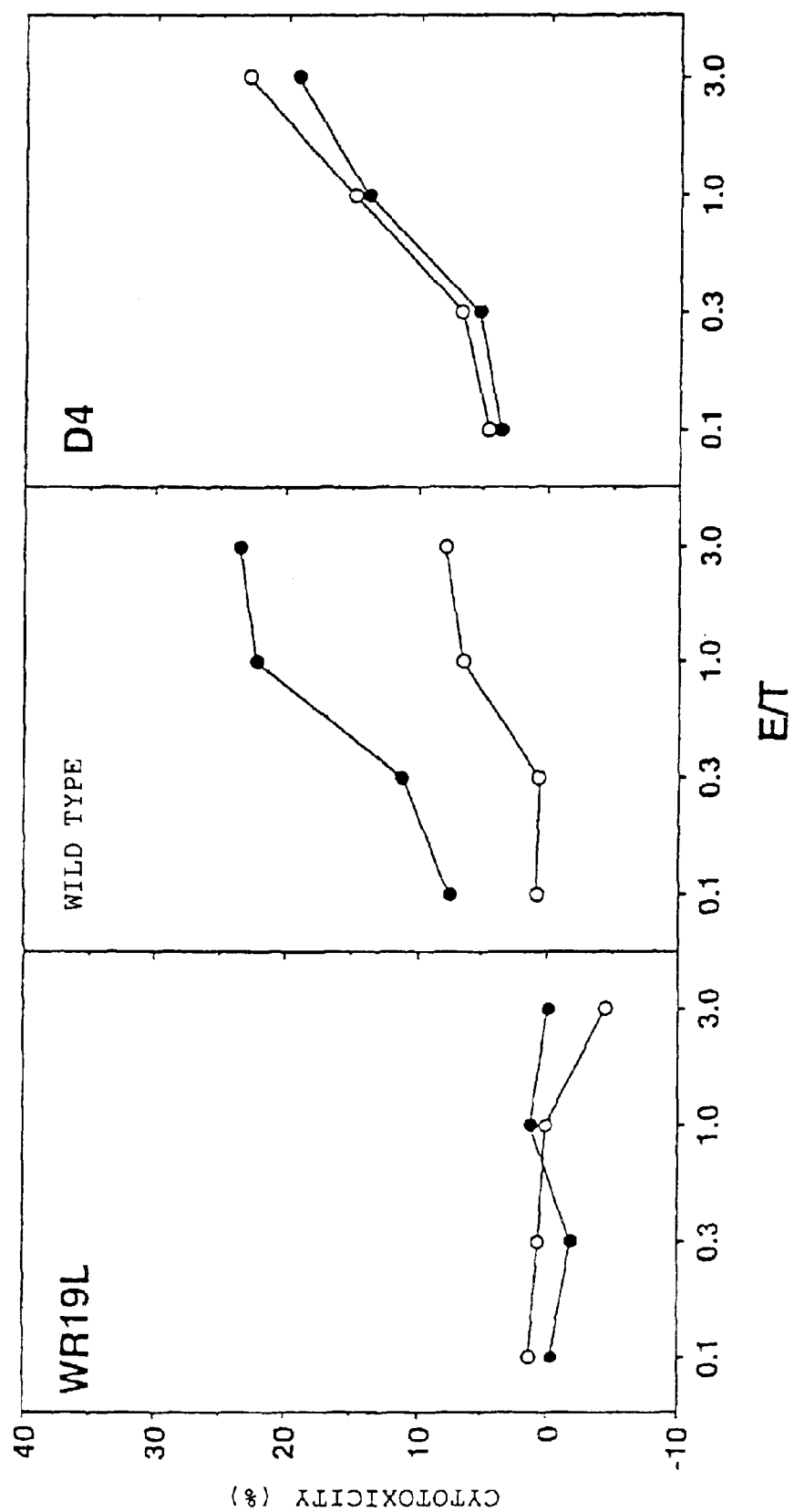

FIG. 6 shows the enhanced cytotoxicity of membrane-bound FasL against human Jurkat cells.

FIG. 7(A) shows the cytotoxic activity of soluble FasL against hepatocytes; FIG. 7(B) shows the cytotoxic activity of FasL against mouse hepatocytes; and FIG. 7(C) shows effects of soluble FasL on the cytotoxic activity of membrane-bound FasL.

BEST MODE FOR CARRYING OUT THE INVENTION

The novel FasL derivative according to the first embodiment of the present invention is a derivative or a mutant of the Fas ligand which has a tolerance, a resistivity or a reduced sensitivity to protease, and in particular, a Fas ligand derivative wherein said protease is a metalloprotease and/or a protease which has the function of shedding the membrane-bound FasL from the cell either in vivo or in vitro, namely, a processing enzyme. More specifically, the FasL derivative is the one which has a mutation of amino acid residue(s)such as deletion, substitution or insertion of one or more amino acids, and in particular, deletion of one ore more, for example, four or more amino acids at or near the cleavage site by the processing enzyme of the natural membrane-bound FasL. The novel FasL derivative of the present invention should include the minimum active region for Fas-binding ability and/or apoptosis-inducing ability in the extracellular region of the FasL, and preferably, the FasL derivative includes the membrane-binding region which enables binding to the cell membranes and other membranes under physiological conditions. As shown in the Examples, inclusion of the entire cytoplasmic region is not necessary. The extracellular region and the membrane-binding region may be linked either directly or indirectly with an intervening region such as linker peptide. The transmembrane region is not necessarily the one derived from natural FasL, and also usable is a membrane-binding substance other than polypeptides and it is also acceptable to bind a substance having other functions such as the substance having polymerizability. An example of the membrane other than the cell membrane is liposome.

Examples of the novel FasL derivative according to the first embodiment of the present invention are those having an amino acid sequence of natural human Fas ligand wherein amino acids 129–130 from N terminal are deleted or substituted, and at least one of amino acids 111–128 and 131–133 from N terminal is deleted or substituted, and those wherein amino acids 8–69 from N terminal are further deleted. Preferred examples are the one having an amino acid sequence described in SEQ ID No. 1; the one wherein amino acids 8–69 from N terminal are further deleted (hereinafter referred to as D4); the one having an amino acid sequence described in SEQ ID No. 2; and the one wherein amino acids 8–69 from N terminal are further deleted (hereinafter referred to as D5). The polypeptide of SEQ ID No. 1 and D4 are those wherein 23 amino acids at 111–133 from N terminal are deleted from natural human Fas ligand, and the polypeptide of SEQ ID No. 2 and D5 are those wherein 4 amino acids at 128–131 from N terminal are deleted from natural human Fas ligand. These polypeptides have amino acid deletion near the site where the metalloprotease cleaves the membrane-bound Fas ligand at Lys 129 and Gln 130 to release soluble Fas ligand. Although the membrane-bound Fas ligand derivatives have deletion mutation, cytotoxicity of these polypeptides are equal to or higher than the natural membrane-bound Fas ligand.

The Fas ligand derivatives of the present invention having the amino acid sequence of natural human Fas ligand wherein amino acids 129–130 from N terminal are deleted or substituted, and at least one of amino acids 111–128 and 131–133 from N terminal is deleted or substituted; the amino acid sequence wherein amino acids 8–69 from N terminal are further deleted; the sequence described in SEQ ID No. 1, D4; and the sequence described in SEQ ID No. 2, D5 as mentioned above as examples are characterized by their high metalloprotease tolerance and metalloprotease resistance as well as reduced sensitivity to metalloprotease. Therefore, these Fas ligand derivatives are uncleavable by metalloprotease and resistant to shedding by metalloprotease, and loss of cytotoxicity is thereby prevented. As a consequence, the Fas ligand derivatives of the present invention are more efficient than natural membrane-bound Fas ligand in their action with the Fas on the surface of the target cell to exhibit higher apoptotic cytotoxicity.

It should be noted that the amino acid sequences shown in SEQ ID No. 1 and 2 have four glycosylation sites (N-glycosylation sites), respectively. In SEQ ID No. 1, amino acid numbers 76–78, 161–163, 227–229, and 237–239, and in SEQ ID No. 2, amino acid numbers 76–78, 180–182, 246–248, and 256–258 correspond to such glycosylation sites. The novel FasL derivative of the present invention may also have a sugar chain added thereto at such site.

When the Fas ligand derivative of the present invention is the one produced by genetic engineering process using yeast, an animal cell, or other eukaryotic cell as a host, the resulting polypeptide may have a sugar chain added thereto. In contrast, when the membrane-bound Fas ligand derivative of present invention is the one produced by genetic engineering process using *E. coli* or other prokaryotic cell as a host, the resulting polypeptide has no such sugar chain.

The Fas ligand derivative of the present invention can be used in inducing apoptosis to remove cells unnecessary for living body. For example, Fas is expressed in the cells infected by AIDS virus, and the Fas ligand derivative of the present invention can be used in the treatment of AIDS by artificially inducing the apoptosis in early stage of AIDS virus infection to thereby remove the infected cells in their early stage. The Fas ligand derivative of the present invention can also be used in some types of autoimmune diseases for removing autoantigen-reactive T cells by artificially inducing Fas-mediated apoptosis. The Fas ligand derivative of the present invention can also be used in cancer treatment. Morimoto, H. et al. has reported that carcinostatic effects of adriamycin and cisplatin can be synergically enhanced by inducing Fas-mediated apoptosis of the cancer cells (Cancer Res., vol. 53, pages 2591–2596, 1993).

The soluble Fas ligand according to the second embodiment of the present invention is not limited to any particular type as long as it shares at least some region with the natural Fas ligand; it is soluble in an aqueous solution in the absence of a surfactant; it functions as a Fas antagonist; and it has the function of regulating the apoptosis. The term, Fas antagonist used herein designates an antagonist to Fas/Fas ligand system which blocks signal generation by Fas or its transmission at some stage by some mechanism to thereby suppress or inhibit the Fas-mediated apoptosis.

The soluble Fas ligand of the present invention is the ligand which shares at least some region with the natural Fas ligand; which is soluble in an aqueous solution in the absence of a surfactant; and which interacts with the extracellular region of the Fas to compete with the natural FasL or to induce downregulation of the Fas. Exemplary such soluble Fas ligand is the one comprising at least some of the extracellular region of the Fas ligand, and a preferable example of the soluble Fas ligand is a polypeptide comprising the amino acid sequence of human natural Fas ligand from Gln 130 from N terminal to the C terminal.

Furthermore, natural membrane-bound Fas ligand and the polypeptide which is cleavable in vivo or in vitro by metalloprotease to become soluble Fas ligand as in the case of natural membrane-bound Fas ligand may be used as a precursor for the soluble Fas ligand of the present invention.

The inventors of the present invention have found that the soluble Fas ligand suppresses FasL-induced cytotoxicity, and in particular, membrane-bound FasL-induced cytotoxicity; and in other words, that the soluble Fas ligand functions as a Fas antagonist or as an apoptosis regulator to suppress, inhibit, or regulate the apoptosis. The present invention has been completed on such finding. Use of the soluble Fas ligand of the present invention which functions as a Fas antagonist has enabled to treat and prevent the FasL-induced apoptosis. The present invention also provides a method for suppressing or regulating the Fas function or apoptosis by using the soluble FasL, and an apoptosis antagonist or regulator containing the soluble FasL.

Involvement of the FasL-inducing apoptosis in CTL-mediated autoimmune diseases such as hepatitis, insulin-dependent diabetes, and thyroiditis (Hashimoto's disease) has been indicated. Apoptosis-involving diseases also include, for example, decrease in immunocompetence in the late stage of AIDS virus infection and liver dysfunction in fulminant hepatitis which are believed to result from significant decrease in the tissue function due to apoptosis of the immunocytes and hepatocytes. Other apoptosis-involving diseases include heart disease, GVHD, renal disease, diseases based on ischemic reperfusion injury and diseases based on organ failure.

Exemplary heart diseases include ischemic heart diseases such as myocardial infarction, myocarditis of various causes, cardiomyopathy, in particular, dilated cardiomyopathy, cardiac insufficiency, and ischemic reperfusion injury and diseases caused by such ischemic reperfusion injury. Exemplary GVHD include GVHD after bone marrow transplantation such as incompatible bone marrow transplantation and bone marrow transplantation in the case of congenital immunodeficiency; GVHD after organ transplantation; GVHD after blood infusion of large amount to the host with reduced immunocompetence. Ischemic reperfusion injuries include ischemic reperfusion injuries found in liver, heart, kidney, lung, spleen, small intestine, large intestine, stomach, pancreas, brain, muscle, skin, and the like as well as diseases caused by such ischemic reperfusion injury such as hepatic insufficiency, reperfusion arrhythmia, renal insufficiency, necrotizing enterocolitis, and other injuries and dysfunction of various organs.

Further apoptosis-involving diseases include diseases caused by ischemic reperfusion injuries as described above, allergic contact dermatitis and articular rheumatism, and MODS associated with SIRS.

Further apoptosis-involving diseases include organ injuries caused by endotoxin, in particular liver injury and endotoxinia as well as sepsis, including not only the acute phase but also chronic injuries.

Other apoptosis-involving diseases of liver include hepatic insufficiency, tissue injury, and liver hypofunction caused by ischemic reperfusion injury in the case of decrease or stopping of the blood flow (blood supply) in surgery such as transplantation, circulation dysfunction or shock. Other apoptosis-involving diseases of heart include irreversible cell death and fatal arrythmia caused by intracellular calcium ion overload resulting from reperfusion after percutaneous transluminal coronary recanalization (PTCR) or percutaneous transluminal coronary angioplasty (PTCA) conducted as a treatment for myocardial infarction. Other apoptosis-involving diseases of kidney include renal failure and injury of cells intrinsic to glomerulus (endothelial cell, epithelial cell, mesangial cells), mesangium matrix, extracellular matrix of basal lamina, or epithelial cell of uriniferous tubule, and the like caused by post-surgery ischemic reperfusion and ischemic reperfusion due to renal transplantation and the like.

The soluble Fas ligand and Fas ligand derivative according to the first and the second embodiments of the present invention can be used in a pharmaceutical composition. In such a case, the pharmaceutical composition may be in the form of an injection or peroral agent or in the form of a kit in adequate combination with at least one medical carrier or mediator such as sterilized water or physiological saline, vegetable oil, mineral oil, higher alcohol, higher fatty acid, non-toxic organic solvent, and the like, and optionally, with additives such as recipient, colorant, emulsifying agent, suspending agent, surfactant, disintegrator, antiadsorbent, stabilizer, preservative, humectant, antioxidant, buffer agent, isotonic agent, pain reliever, and the like. Preferably, the prophylactic or treating agent of the present invention is administered parenterally, for example, by intravenous injection, coronary injection, intramuscularly injection, intraperitoneal injection, or hypodermic injection, and either systemically or topically, and rapidly or continuously. Although the amount of the prophylactic or treating agent of the present invention administered to human patient may vary depending on such factors as the disease conditions, the age, and the method of administration, administration of an adequate amount at an adequate occasion is necessary. For example, in the case of systemic administration, divided dose may be selected in the range of about 0.1 to about 100 mg/kg. However, the use of the pharmaceutical composition of the invention is not limited to the method and the dose of administration as described above, and use in combination with other pharmaceutical is also acceptable.

When the Fas ligand according to the first or the second embodiment of the present invention is used for a pharmaceutical composition, the composition may be formulated by any one of the conventional methods. For example, preparation for injection may be the one prepared by dissolving the purified Fas ligand according to the first or the second embodiment of the present invention in a solvent such as physiological saline or a buffer which is optionally supplemented with an anti-adsorption agent and the like. The preparation for injection may also be in the lyophilized form which is the preparation in solution form further lyophilized for reconstitution before its use. Such lyophilization can be carried out with the aid of an excipient commonly used in the art.

The Fas ligand according to the first and the second embodiment of the present invention is not limited for its method of production. For example, the Fas ligand may be prepared by chemical synthesis with a peptide synthesizer (for example, peptide synthesizer model 430A, manufactured by Perkins Elmer Japan K. K.).

Also, the Fas ligand may be purified from tissue, cell, or body fluid of human or organism other than human. Exemplary body fluids of human and other animals include blood and urine. The cell used may be adequately selected from the cells that produce the novel polypeptide of the present invention. Exemplary cells include cells such as splenocytes, thymocytes, and lymphocytes, and cell lines thereof, and the cells may be selected by conducting northern blot or western blot analysis and the like, and selecting the one exhibiting high yield of the novel polypeptide of the present invention.

If necessary, the polypeptide may be produced by inducing its production through stimulation of the cells with one or more stimulants selected from PMA (phorbol myristate acetate), ionomycin, PHA (phytohemagglutinin), ConA (concanavalin A), and IL-2 (interleukin-2), and purifying the polypeptide of interest from the cell lysate or the culture medium. The purification may be conducted by adequately combining concentration, chromatographic process, salting out, or any of other polypeptide purification processes commonly used in the art and using the binding activity to Fas or cytotoxicity to the Fas-expressing cell as an index.

The Fas ligand according to the first and the second embodiment of the present invention, however, is preferably the one prepared by genetic engineering process, namely, a recombinant polypeptide in view of the purity. The production of the polypeptide of interest can be accomplished by inserting cDNA of the Fas ligand according to the first or the second embodiment of the present invention or the DNA of the present invention in an adequate vector and obtaining a recombinant gene; transforming a host cell with the resulting recombinant gene; and culturing the resulting transformant to recover the culture mixture which is purified to obtain the polypeptide of interest. Another exemplary method is a cell-free synthesis using the DNA or recombinant DNA molecule as described above (Sambrook, J. et al.: Molecular Cloning, a Laboratory Manual, 2nd ed. Cold Spring Harbor Laboratory, New York (1989)).

The novel DNA according to the third embodiment of the present invention is the DNA coding for the novel Fas ligand derivative of the present invention, and in particular, the amino acid sequence described in SEQ ID Nos. 1 and 2 or D4 and D5. The DNA of the present invention is not limited for its sequence as long as it encodes the novel Fas ligand derivative of the present invention. It has been known that there are 1 to 6 DNA triplets corresponding to each amino acid, and the nucleotide sequence coding one peptide is not limited to one type. The codon usage is not limited to any particular type as long as it codes the same amino acid.

The DNA of the present invention may be either a cDNA or a chromosomal DNA including the intron as long as it includes the nucleotide sequence coding for the novel Fas ligand derivative of the present invention. The novel DNA of the present invention, however, is preferably a cDNA in view of the ease of incorporation into the vector and other handling conveniences in the genetic engineering process. Exemplary such cDNA are those having the nucleotide sequence described in SEQ ID Nos. 4, 5 and 6.

The novel DNA of the present invention may be either in the form of a single stranded DNA or a double- or triple-stranded DNA hybridized with a DNA or RNA having the complimentary sequence.

The sequence of RNA and complimentary DNA and RNA will be uniquely determined from the nucleotide sequence of the DNA of the present invention.

The DNA of the present invention may be used for producing the novel Fas ligand derivative of the present invention by recombinant DNA technology. To be more specific, the DNA of the present invention may be inserted in an appropriate position of an expression vector including the promoter sequence and other sequences required for the expression, and transforming an appropriate host cell with this vector for expression of the novel Fas ligand derivative of the present invention from the transformant. The DNA of the present invention may be also used in gene therapy of the diseases associated with genetic deficiency of apoptotic mechanism such as cancer, virus diseases, and autoimmune diseases by incorporating the novel DNA of the present invention in an appropriate vector and administrating the vector to the patient. The DNA of the present invention may be also used in cell therapy wherein the cell of a cell line or the cell taken out from the living body is transformed with the DNA of the present invention, and the transformed cell is placed back in the living body. The DNA of the present invention may be also used in producing a transgenic animal for use in providing a FasL derivative-expressing organ or tissue adapted for use in transplantation.

Furthermore, the novel DNA of the present invention may be also used in developing an antisense drug, in producing a transgenic mouse and other model animals of the apoptosis-involving diseases, and in diagnosing the apoptosis-involving diseases by assaying the expression of the Fas ligand and its derivative in tissues after enzymatic marking.

The novel DNA of the present invention may be obtained by chemical synthesis or from a DNA library.

The novel DNA of the present invention may be chemically synthesized, for example, by dividing the DNA having the desired nucleotide sequence into fragments of about 20 bases and synthesizing each fragment in a DNA chemosequencer (for example, model 394, manufactured by Perkin Elmer Japan K. K.), optionally phosphorylating the 5' end, and annealing and ligating the fragments to obtain the DNA of interest.

When the novel DNA of the present invention is obtained from a DNA library, an appropriate genome DNA library or cDNA library is screened by hybridization screening method or immunoscreening method utilizing an antibody, the clone having the desired DNA is amplified, and the desired DNA is recovered by enzymatic cleavage.

The novel DNA of the present invention can be also obtained by means of PCR (Polymerase Chain Reaction) wherein the genome DNA library of the cDNA library is used for the template.

An embodiment of the present invention was carried out under the conditions as described below.

(1) Production and Purification of Human Soluble FasL

Hamster anti-human FasL monoclonal antibody (clone 4H9) has been described in Tanaka et al., Nature Med. 2, 317–322, 1996. The antibody (10.5 mg) in 3.5 ml of phosphate-buffered saline (PBS) was mixed with 5 ml protein A-Sepharose 4FF beads (Pharmacia, Uppsala, Sweden), and incubated for 1 h at 4° C. The beads were extensively washed with Tris-buffered physiological saline (TBS, 50 mM Tris-HCl, pH 7.4, 150 mM NaCl), and once with 200 mM sodium borate buffer (pH 9.0) to remove the unbound proteins. The bound antibody was then covalently conjugated to the beads by incubating with 20 mM dimethylpimerimidate in 200 mM sodium borate buffer.

Mouse WR19L cell transformants expressing human FasL (1A12 cell) have been described in Tanaka et al., Nature Med. 2, 317–322, 1996. The 1A12 cells ($1 \times 10^5$ cells per ml) were cultured for 3 days in RPMI 1640 medium supplemented with 5% FCS, and about 2 liters of the culture medium were collected. Proteins in the medium were concentrated by ammonium sulfate precipitation (50–70%), and dialyzed against PBS. The proteins were then applied to a column (1 ml) of anti-FasL antibody-conjugated protein A-Sepharose, which was equilibrated with PBS. The column was washed with 20 ml of 50 mM Tris-HCl buffer, pH 8.6, containing 150 mM NaCl, and FasL bound to the column (anti-FasL antibody) was eluted with 50 mM glycine-HCl buffer (pH 2.2) containing 150 mM NaCl. The eluents were immediately neutralized with 1M Tris-HCl (pH 7.5), dialyzed against PBS, and concentrated using a Centricon apparatus (Amicon Corp., Beverly, Mass.).

To determine the N-terminal amino acid sequence, 6 μg of the purified FasL was separated by electrophoresis on a 10–20% polyacrylamide gel (Daiichi Pure Chemical, Tokyo) in the presence of 0.1% SDS. Proteins were electroblotted onto a PVDF membrane at 30V for 16 hours as described in Fukunaga et al., J. Biol. Chem., 265, 14008–14015, 1990 except that the blotting buffer contained 0.075% SDS, stained with Coomassie brilliant blue, and its N-terminal amino acid sequence was determined by Edman degradation at Takara Shuzo Co.

(2) Establishment of the Transformants Expressing Various Mutants of Human FasL

The expression plasmid (pBOSHFLD1) for human FasL lacking a cytoplasmic region (amino acids 8–69) has been described in Tanaka et al., Nature Med. 2, 317–322, 1996. Expression plasmids (pBOSHFLD4, pBOSHFLD5, and pBOSHFLD6) for human FasL mutants carrying a series of deletion and point mutations at the cleavage site were generated by means of recombinant PCR using pBOSHFLD1 as a template. In brief, to construct pBOSHFLD4 carrying a deletion of the amino acids from 111 to 133, the 5' portion of FasL cDNA was amplified using a sen (BOS6; CCTCAGACAGTGGTTCAAAG) (SEQ ID No: 7) containing a sequence from the pEF-BOS vector (Mizushima, Nagata, Nucleic Acids Res., 18, 5322, 1990) and an antisense deletion primer (DA4; TTTTCAGGGGGTGGACTGGGCTCCTTCTGTAGGTGGAAG (SEQ ID No: 8), a sequence coding for amino acids 105–110 and 134–139 of human FasL). The 3' portion of the cDNA was amplified using a sense primer (DS4) complementary to the DA4 primer and a primer (HFLP3; GCTCTAGAACATTCTCGGTGCCTGTAAC) (SEQ ID No: 9) containing a sequence from the 3' noncoding region of FasL cDNA. The PCR was carried out under the conditions described in Takahashi et al., Cell, 76, 969–976, 1994. The primary PCR products were purified by agarose gel electrophoresis, mixed 1:1, then amplified by secondary PCR with primers BOS6 and HFLP3. The resultant DNA fragment was digested with XbaI and inserted into the pEF-BOS vector. Other deletion or point mutants were constructed by a similar procedure using the following oligonucleotides as primers: DA5 (TGGACTGGGGTGGCCCAAAGATGATGCTGT) (SEQ ID No: 10) and DS5 (complementary to DA5) for pBOSHFLD5 (deletion of amino acids from 128 to 131), and DA6 (GGGGTGGCCTATTTGTGCCTCCAAAGATGATGC) (SEQ ID No: 11) and DS6 (complementary to DA6) for pBOSHFLD6 (substitution of Lys-129 for Ala). Mouse WR19L cells were cotransfected by electroporation with the expression plasmid together with pPUR, which carries the puromycin-resistant gene (manufactured by Clontech) (Ito et al., Cell, 66, 233–243, 1991). The puromycin-resistant transformants were selected with 800 ng/ml puromycin, and the transformant clones expressing human FasL were selected by FACS analysis using biotinylated anti-human FasL antibody (4H9) for flow cytometry and PE-conjugated streptavidin (manufactured by Becton Dickinson).

(3) Assay for Cytotoxic Activity

The cytotoxic activity of human soluble FasL for Fas-expressing W4 or Jurkat cells was determined by means of the MTT method as described in Tanaka et al., EMBO J., 14, 1129–1135, 1995. The cytotoxic activity of the FasL-expressing transformants for W4 or Jurkat cells was determined by a $^{51}$Cr-release assay, essentially as previously in Suda et al., Cell, 75, 1169–1178, 1993. In brief, W4 or Jurkat cells ($1 \times 10^4$) were labeled with $^{51}$Cr and mixed with the FasL transformants at various ratios. After incubation at 37° C. for 4 h, the specific release of $^{51}$Cr from the target cells was determined.

The cytotoxic activity of soluble FasL or FasL transformants for primary hepatocytes was determined as follows. Mouse hepatocytes were prepared from 11-week-old female C3H/He mice (purchased from SLC, Shizuoka) as described in Adachi, Nature Genet. 11,294–300,1995. Hepatocytes ($1 \times 10^5$ cells) were seeded on 48-well plates coated with 0.03% type I collagen, and cultured in DMEM containing 5% FCS for 24 h. The hepatocytes were incubated at 37° C. for 22 h with soluble FasL or the FasL transformants. The GOT levels released into the culture medium were measured using Transaminase CII-test kit manufactured by Wako Chemicals.

(4) Immunoprecipitation and Western Blotting

The FasL transformants were cultured in RPMI 1640 medium containing 10% FCS, and FasL in the culture medium and the cell lysates were analyzed by immunoprecipitation followed by western blotting. In brief, the cells were lysed by incubation on ice for 30 min in TBS containing 1% NP40, 1 mM (p-amino-phenyl)methane sulfonyl fluoride hydrochloride, 1 μg/ml of pepstatin, and 1 μg/ml of leupeptin. After centrifugation at 15,000 r.p.m. for 20 min, the supernatant fraction was collected for immunoprecipitation. The cell lysates (100 μl) from $4 \times 10^5$ cells or 100 μl of the culture medium were preadsorbed to 25 μl of protein A-Sepharose 4FF beads (Pharmacia) for 45 min at 4° C., followed by incubation overnight at 4° C. with 10 μl of the anti-FasL monoclonal antibody (4H9)-conjugated protein A-Sepharose. The beads were extensively washed with TBS containing 0.1% NP40, and suspended in 10 µl of Laemmli's sample buffer without β-mercaptoethanol. Samples were fractionated by electrophoresis on 10–20% gradient polyacrylamide gels, and the proteins were transferred to PVDF membranes (manufactured by Millipore) at 30 V for 15 h at 4° C. FasL protein was detected by western blotting with the anti-FasL polyclonal antibody as described in Tanaka et al., EMBO J., 14,1129–1135,1995.

The results obtained in the Examples are shown in Table 1, below and FIGS. 1 to 7.

Table 1 shows the results of the production of human soluble FasL by transformants expressing wild-type and mutant FasL.

TABLE 1

| Constructs | Clones | Cytotoxic activity (units/ml) |
|---|---|---|
| Wild | 1A12 | 1667 |
|  | 1F10 | 556 |
| D4 | 41B | <20 |
|  | 44D | <20 |

Mouse WR19L cell transformant clones expressing wild-type FasL, the deletion mutants (D4 or D5), or the point mutation mutant (D6) of FasL were cultured at 37° C. for 24 h in the presence of 20 µM BB-2116. The cells were then cultured at 37° C. for 24 h in the absence of BB-2116 at a concentration of $4 \times 10^5$ cells/ml. The cytotoxic activity of the supernatant was then determined by the MTT assay using mouse W4 cells as a target. One unit of the cytotoxicity was defined as the dilution that gave half-maximal cytotoxicity against $7.5 \times 10^4$ cells in 100 µl.

Figure 1:
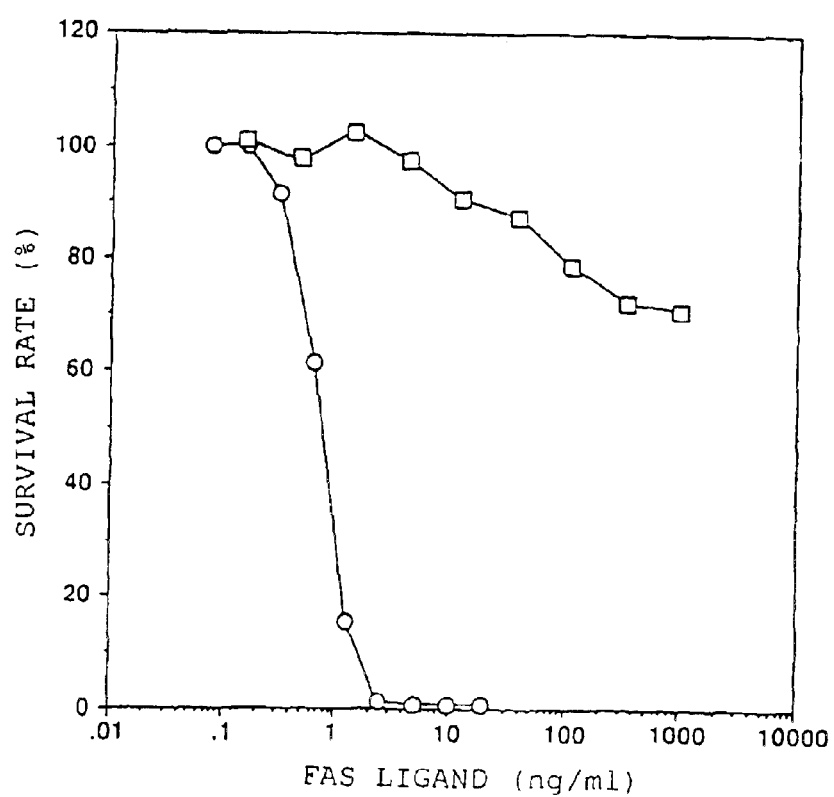
FIG. 1 is view showing purified human soluble Fas ligand.

FIG. 1 shows purified human soluble Fas ligand.

(A) is the results of the analysis by SDS-polyacrylamide gel electrophoresis. The purified human soluble FasL (6 µg) was analyzed by electrophoresis on a 10–20% gradient polyacrylamide gel in the presence of 0.1% SDS, and stained with Coomassie brilliant blue. As size markers, molecular mass standards (Rainbow™ colored protein markers, manuractured by Amersham) were run in parallel (M), and the sizes of the standard proteins are shown in kilodaltons (kD). (B) is the cytotoxic activity of soluble FasL. Mouse W4 or human Jurkat cells ($7.5 \times 10^4$) were incubated in a 96-well microtiter plate at 37° C. for 15 h with the indicated concentrations of soluble FasL. The cell viability was determined using the MTT assay, and is expressed as the percentages of the viability observed in the absence of FasL.

FIG. 2 is a schematic diagrams of the FasL constructs carrying deletion or point mutation.

The structures of the wild-type human FasL (wild), its deletion mutants (D4 and D5) and point mutants (D6) are schematically shown. CYT, TM and EXT represent the cytoplasmic, transmembrane and extracellular regions of human FasL, respectively. The amino acid sequence (EKQI) at the cleavage site of human FasL is shown. In the D4 and D5 constructs, the amino acids 111–133 and 128–131 were deleted, respectively. In the D6 construct, Lys was substituted for Ala at codon 129.

FIG. 3 shows lack of shedding of soluble FasL by human FasL deletion mutants.

FIG. 3 shows immunodetection of human FasL in the transformant cells. The parental WR19L cell (WR19L) or its transformant expressing either wild-type human FasL (wild), or the D4, D5, or D6 mutant forms of FasL were cultured for 24 h at a concentration of $4 \times 10^5$ cells/ml in medium containing 20 µM BB2116. The cells were then shifted to medium lacking BB2116, and further incubated for 24 h. The cell lysates (C) and the medium (S) from each transformant were subjected to immunoprecipitation with an anti-human FasL monoclonal antibody (4H9). The immunoprecipitates were analyzed by western blotting using rabbit anti-human FasL antibody as described above. As size markers, molecular mass standards (Rainbow markers, manufactured by Amersham) were run in parallel, and the sizes of the standard proteins are shown in kilodaltons (KD).

FIG. 4 shows expression of FasL on the cell surface. Mouse WR19L cell transformants expressing wild-type FasL (clones 1A12 and 1F10) or D4 (clones 41B and 44D), D5 (clones 59A and 5-2-21) or D6 (clone 61B and 617C) mutant FasL were cultured for 24 h in medium with (dotted lines) or without (solid lines) 20 µM BB2116. The cells were stained by biotinylated 4H9 anti-human FasL antibody and PE-conjugated streptavidin, and analyzed by flow cytometry as described above.

FIG. 5 shows the ability of the membrane-bound FasL to kill mouse W4 cells overexpressing Fas.

The cytotoxic activities of parental WR19L cells (○), and their transformants expressing the wild-type (clone 1F10, ●) and D4 mutant (clone 44D, □) FasL were determined by using $^{51}$Cr-labeled W4 as a target at the indicated ratios of effector/target (E/T) cells.

FIG. 6 shows the enhanced cytotoxicity of membrane-bound FasL against human Jurkat cells. The parental mouse WR19L cells (WR19L) and their transformants expressing wild-type human FasL (clone 1F10) or D4 mutant FasL (clone 44D) were cultured for 24 h with (●) or without (○) 20 µM of BB2116. Their cytotoxic activity was then assayed using $^{51}$Cr-labeled human Jurkat cells as a target at the indicated E/T ratios as described above.

Figure 7:
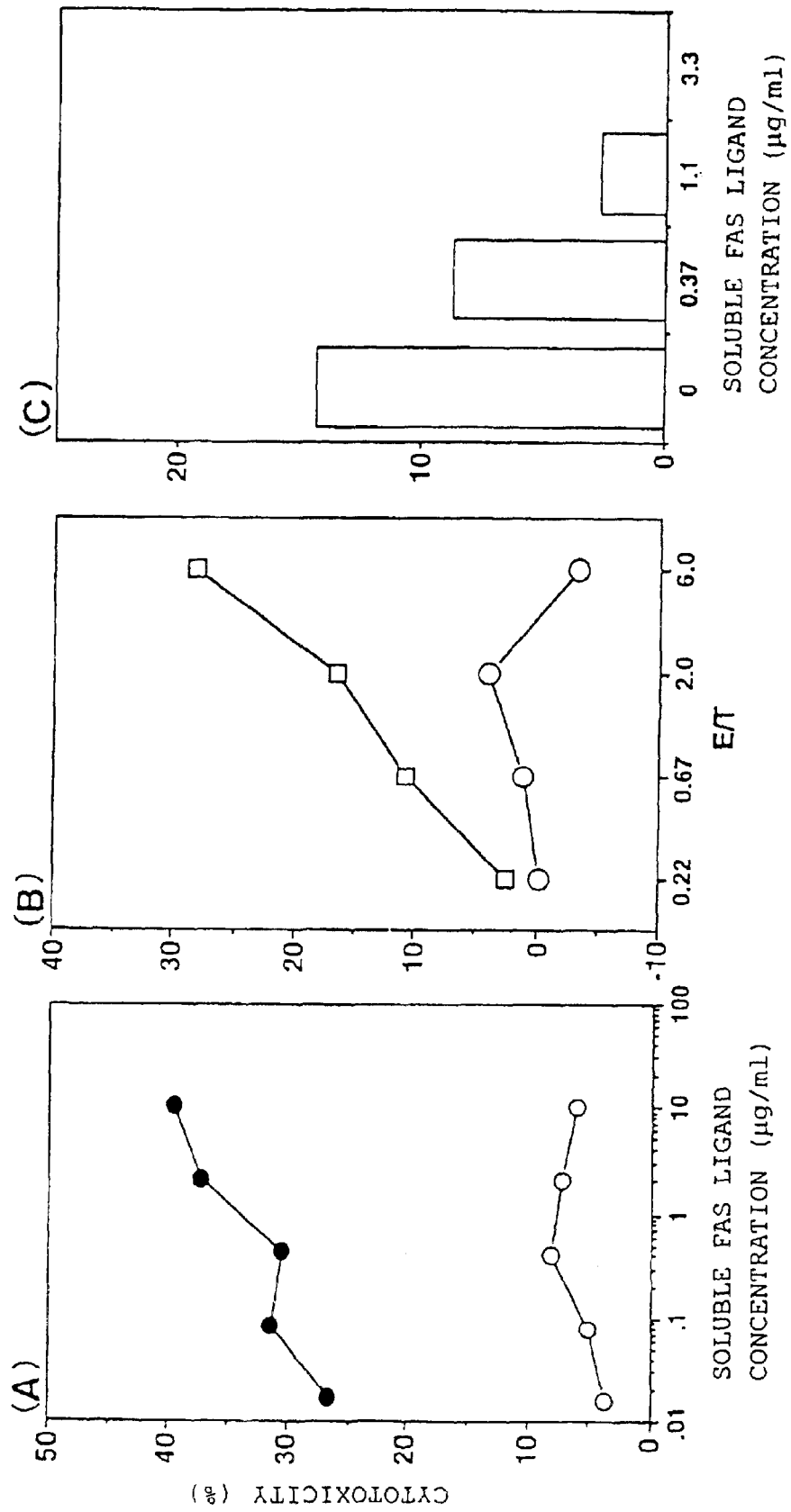

FIG. 7 shows the sensitivity of mouse hepatocytes to the soluble and membrane-bound forms of FasL. (A) shows the cytotoxic activity of soluble FasL against hepatocytes. Primary mouse hepatocytes were incubated at 37° C. for 22 h with the indicated concentrations of human soluble FasL in the presence ( ) or absence (○) of 10 µg/ml of cycloheximide. After incubation, the GOT levels in the medium were measured by means of a kit. Total GOT activity was determined in the cell lysates after lysing the cells with 0.1% NP40. The specific killing is expressed as percentage of the released GOT levels of the total GOT activity. (B) shows the cytotoxic activity of membrane-bound FasL transformants against mouse hepatocytes. Mouse hepatocytes were incubated at 37° C. for 22 h with WR19L cells (○) or the D4 mutant (clone D44, □) at the indicated E/T ratios. After incubation, the killing activity was determined as described above. (C) shows inhibition of the cytotoxic activity of membrane-bound FasL by soluble FasL. Mouse hepatocytes were incubated at 37° C. for 22 h with the WR19L cell transformant expressing the D4 mutant at an E/T ratio of 2.0 in the presence of the indicated concentrations of soluble FasL. After incubation, the specific killing activity was determined as described above.

<Purification of Human Soluble Fas Ligand>

The inventors of the present invention have previously established a stable transformant line (1A12 cells) that constitutively expresses human FasL on its cell surface, and also releases functional soluble FasL into the culture medium (Tanaka et al., Nature Med. 2, 317–322, 1996). To purify human soluble FasL, 1A12 cells were cultured in PRMI medium containing 5% FCS, and FasL was affinity-purified with anti-FasL antibody (4H9)conjugated with protein A-Sepharose. About 200 μg of purified FasL was obtained from 2000 ml conditioned medium. As shown in FIG. 1a, polyacrylamide gel electrophoresis of the purified FasL showed a single band at the molecular mass of 26,000, which is similar to the size of soluble FasL produced by activated human peripheral blood lymphocytes (Tanaka et al., EMBO J., 14, 1129–1135, 1995). When the cytotoxic activity of the purified FasL was assayed using the Fas-expressing mouse W4 cells as a target, it had a specific activity of $2 \times 10^7$ U/mg, which was essentially identical to that of the recombinant soluble FasL produced in Pichia Pastoris (Tanaka et al., J.Immunol., 158, 2303–2309, 1997). Human Jurkat cells express Fas endogenously and are sensitive to anti-Fas antibody-induced apoptosis (Takahashi et al., Eur.J.Immunol., 23, 1935–1941, 1993). When the cytotoxic activity of the soluble FasL was assayed using the Jurkat cells as a target, it showed very weak activity. The soluble FasL killed only 30% of the cells after incubation with 1 μg/ml soluble FasL for 15 hours, and it was then indicated that the Jurkat cell is more than 1000 times less sensitive to the soluble FasL under the same condtions compared to mouse W4 cell.

<The Cleavage Site of FasL>

To determine the N-terminal amino acid sequence of the purified soluble FasL, the protein was separated by electrophoresis on a polyacrylamide gel, and then transferred to a PVDF membrane. The Edman degradation of the purified 26-kDa protein by means of an automated sequencer yielded a single sequence of Gln-Ile-Gly-His-Pro-Ser-Pro-Pro (SEQ ID No: 12). This sequence exactly corresponds to the sequence of human FasL from amino acids 130 to 137. From these results, the inventors of the present invention concluded that human FasL synthesized as a membrane-bound form is cleaved between Lys 129 and Gln 130 to create a soluble form.

<Establishment of Cells Expressing Noncleavable FasL>

To establish transformants expressing noncleavable FasL, expression plasmids for a series of deletions or point mutations at the cleavage site were constructed. D4 and D5 are FasL deletion mutants in which the amino acids–19 to +4 and –2 to +2 were deleted, respectively. The D6 construct has a point mutation that consists of a substitution of Lys 129 for Ala. The mutated genes were placed under the promoter of human elongation factor (pEF) 1α gene and introduced into mouse WR19L cells.

To examine whether the mutated FasL could be cleaved, each transformant was cultured for 24 hours in a medium containing a metalloproteinase inhibitor BB2116, then switched to the medium without the inhibitor. After culturing the cells for 24 hours, the FasL activity and FasL protein in the culture medium were analyzed. As shown in Table 1, the transformants of FasL carrying the intact cleavage site secreted a high level of FasL into the medium. The mutant with a 23-amino acid deletion at the cleavage site (CD4) did not produce any cytotoxic FasL activity, and the 4-amino acid deletion mutant (CD5) produced little if any cytotoxic activity. The point mutant from Lys to Ala at –1 still produced soluble FasL. The culture medium and cell lysates of the transformants were then immunoprecipitated with the anti-human FasL monoclonal antibody (4H9), and the immunoprecipitates were analyzed by western blotting using the anti-human FasL polyclonal antibody. As shown in FIG. 2B, the cell lysates from each FasL transformant showed a major band of 32–35 kDa, which can be expected from the size of the deletion. The culture medium from the wild-type and point mutants (D6) contained soluble FasL with the molecular weight of 26000, whereas no soluble FasL was detected in the medium from the transformants expressing the deletion mutants (CD4 and CD5). These results agree with the detection of FasL activity in the medium from wild-type and D6 mutant, but not from D4 and D5 mutants.

To confirm the resistance of the mutant FasL against proteolytic cleavage, the inventors of the present invention examined FasL expression on the cell surface by flow cytometry. As shown in FIG. 4, all transformants expressed a high level of FasL on their cell surfaces when they were cultured in the presence of BB2116. The expression level of FasL on the cell surface greatly decreased (to about ⅒th), when the transformants expressing intact FasL or the substitution mutant were cultured in the absence of BB2116. On the other hand, the transformants bearing the deletion mutants (CD4 and CD5) showed only a slight decrease in FasL on their cell surfaces under the same conditions. These results indicated that the sequence EKQI at the cleavage site in the extracellular region of FasL is essential for the cleavage of membrane-bound FasL. However, a single-substitution mutation at –1 had no effect on its cleavage, indicating that the amino acid at –1 (Lys) is not important for cleavage.

<Enhanced Cytotoxic Activity of the Membrane-bound FasL>

The inventors of the present invention then studied whether or not the membrane-bound FasL that cannot be cleaved to soluble FasL is functional. As shown in FIG. 5, the transformants expressing the cleavable or noncleavable (wt or D4 mutant) FasL showed similar cytotoxic activity for W4 cells, indicating that membrane-bound FasL is active, and that the deletion of 23 amino acids in its cleavage site does not affect the ability of FasL to induce apoptosis by binding to Fas.

The cytotoxicity of these transformants was then determined using Jurkat cells as a target. As shown in FIG. 6, when the transformants expressing intact FasL were used as effectors, their cytotoxic activity was very low, whereas when the D4 transformants expressing the noncleavable FasL were used as effectors, they efficiently killed Jurkat cells. The sensitivity of Jurkat cells to membrane-bound FasL was comparable to or slightly less than that of W4 cells. About 50% of the W4 cells were specifically killed at an E/T ratio of 5.0 whereas 20% or more of the Jurkat cells were killed at an E/T ratio of 3.0. These results indicated that membrane-bound FasL has more potent latent cytotoxicity than soluble FasL, at least against human Jurkat cells. Accordingly, when the transformants expressing the intact FasL were pretreated with BB2116, they showed a strong cytotoxicity for Jurkat cells, which was similar to that observed with the noncleavable D4 mutant (FIG. 6).

To confirm the greater cytotoxicity of the membrane-bound FasL versus the soluble form, we then used mouse primary hepatocytes as a target. Mouse hepatocytes express Fas and can be killed by an agonistic anti-Fas antibody, Jo2, in the presence of cycloheximide (Ni et al., Exp.Cell Res., 215, 332–337, 1994). When soluble FasL was used as a cytotoxic effector, a similar result was obtained; that is, soluble FasL showed little cytotoxicity against hepatocytes, but it caused cell death in the presence of 10 μg/ml cycloheximide (FIG. 7A). Yet when transformants expressing the noncleavable deletion mutant FasL (D4) were used as effectors, they efficiently killed the hepatocytes without cycloheximide (FIG. 7B). Similarly, although transformants expressing the cleavable FasL (wt) showed a weak cytotoxicity against hepatocytes, their cytotoxicity was greatly increased by pretreatment of the effector cells with BB2116 (data not shown).

<The Inhibitory Effect of the Soluble FasL>

As described above, the transformants of the intact FasL expressed a significant level of the membrane-bound form of FasL (FIG. 3), yet their cytotoxic activity was low (FIG. 6). These results suggest that soluble FasL produced by this transformant may have worked as an inhibitor for cytotoxicity. To examine this possibility, hepatocytes were pretreated with various concentrations of soluble FasL, then the sensitivity of the hepatocytes against the membrane-bound form of FasL (D4 mutant) was assayed. As shown in FIG. 7C, soluble FasL inhibited the cytotoxic activity in a dose-dependent manner, and 0.4 μg/ml of soluble FasL was sufficient to block half of the cytotoxic activity at an effector/target (E/T) ratio of 2.0.

In the present invention, human soluble FasL was produced in a mouse T-cell line transformed by a human FasL expression plasmid. Determination of the N-terminal amino acid sequence of the purified human FasL revealed that human soluble FasL is released as a result of cleavage between Lys 129 and Gln 130. The amino acid sequence (Glu-Lys-Gln-Ile) (SEQ ID No: 13) around the cleavage site of FasL is conserved among humans, rats, and mice (Takahashi et al., Int.Immunol., 6, 1567–1574, 1994), and the deletion of 4 to 23 amino acids around the cleavage site prevented the release of human soluble FasL into the culture medium. These results indicate the importance of the amino acid sequence around the cleavage site for the protease that recognizes and cleaves the FasL.

Among the TNF family members that are synthesized as type II membrane proteins, TNF-α and CD40 ligand have been shown to become cleaved to soluble forms (Perez et al., Cell, 63, 251–258, 1990; Pietravalle et al., J.Biol. Chem., 271, 5965–5967, 1996). The cleavage sites of TNF-α and CD40 ligand are Leu-Ala-Gln-Ala/Val-Arg-Ser-Ser (SEQ ID No: 14) and Asn-Ser-Phe-Glu/Met-Gln-Lys-Gly (SEQ ID No: 15), respectively (Aggarwal et al., J.Biol.Chem., 260, 2345–2354, 1985; Graft et al., Eur.J.Immunol., 25, 1749–1754, 1995). These sequences do not appear to be similar to the FasL sequence (Ser-Leu-Glu-Lys/Gln-Ile-Gly-His (SEQ ID NO: 16), indicating that TNF-α, FasL and CD40 ligand are cleaved by distinct proteases with different substrate specificities. However, the shedding of both FasL and TNF-α is blocked by a matrix metalloproteinase (MMP) inhibitor (BB-2116) (Gearing et al., Nature 370, 555–557, 1994; McGeeham et al., Nature, 370, 558–561, 1994; Mohler et al., Nature, 370, 218–220, 1994; Tanaka et al., Nature Med. 2, 317–322, 1996), suggesting that proteases cleaving TNF-α and FasL carry a similar active site. Recently, a protease (TNF-α-converting enzyme, TACE) that cleaves TNF-α has been identified and shown to be a member of the ADAM family proteases which are membrane proteins having a disintegrin and metalloprotease domain (Black et al., Nature 385, 729–733, 1997; Moss et al., Nature, 385, 733–736, 1997). So far, more than 10 members in this family have been identified (Howard et al., Biochem.J., 1996; Wolfsberg et al., Develop.Biol., 169, 378–383, 1995; Yagami et al., Nature, 377, 652–656, 1995). Some of these are specifically expressed in the testis or muscle, and have a specific function, whereas others are expressed almost ubiquitously and have unknown functions. It is likely that the protease that cleaves FasL is also a member of the ADAM family of proteases. A 12 amino acid peptide that carries the sequence around the TNF-α cleavage site was successfully used to characterize and purify TACE (Black et al., Nature 385, 729–733, 1997; Moss et al., Nature, 385, 733–736, 1997). The information on the cleavage site of human FasL, revealed by this study, will allow the inventors of the present invention to design a peptide substrate that can be used to characterize the protease responsible for the cleavage of FasL.

As demonstrated with TNF-α and CD40 ligand (Perez et al., Cell, 63, 251–258, 1990; Pietravalle et al., Eur.J.Immunol., 26, 725–728, 1996), membrane bound FasL was functional, confirming that FasL does not have to enter the cells to execute its function. It is known that the binding of FasL to Fas induces the formation of Death-Inducing Signaling Complex (DISC), which contains the Fas, as well as several signaling components such as FADD and FLICE, and kills the cells. Here, the inventors of the present invention have found that some cells have different sensitivities to the soluble and membrane-bound forms of FasL. Mouse W4 cells that overexpress Fas could be efficiently killed by soluble FasL, but human Jurkat cells or mouse primary hepatocytes that express a moderate level of Fas endogenously were resistant to human soluble FasL. However, Jurkat cells and hepatocytes were efficiently killed by membrane-bound FasL. How can this phenomenon be explained? When TNF binds to its receptor, the TNF/TNF receptor complex is internalized and degraded, which causes downregulation of the receptor (Tsujimoto et al., Pro.Natl.Acad.Sci., 82, 7626–7630, 1985; Watanabe et al., J. Biol. Chem., 263, 10262–10266, 1988). A similar internalization and degradation of Fas may be also observed in FasL/Fas system. The soluble FasL/Fas complex may be easily internalized, whereas the internalization of membrane-bound FasL with Fas is likely to be retarded. Recently, Medema et al. (Medema et al., EMBO J., 16, 2794–2804, 1997) reported that FLICE, one of the earliest signal transducers of Fas-induced apoptosis, is activated only in the DISC at the plasma membrane. If Fas is quickly internalized with soluble FasL, the activation of FLICE by soluble FasL may be minimal, whereas the DISC induced by membrane-bound FasL remains longer and results in higher levels of FLICE activation. W4 cells express Fas in a number far more than Jurkat cells and hepatocytes do, and sum of weak signals are sufficient to kill the cells. Furthermore, if soluble FasL causes a rapid downregulation of Fas, it would inhibit the cytotoxic activity of membranbound FasL. The inventors of the present ivnentio think the above explanation is likely, although the presence of another molecule (or molecules) (other than membrane-bound FasL) in the membrane that costimulates Fas-induced apoptosis cannot be ruled out.

The inventors of the present invention have recently shown that when transgenic mice expressing the human HBV envelope gene in their liver were injected with a small amount ($3 \times 10^6$ cells) of a CTL clone recognizing the envelope protein, the mice developed hepatitis and died in a Fas dependent manner (Kondo et al., Nature Med., 3, 409–413, 1997). Yet a high level of the recombinant soluble FasL was required to show a similar effect (Tanaka et al., 158, 2303–2309, 1997). One of the explanations can be that membrane-bound FasL is the functional form of FasL in vivo. Similar findings have been previously reported for TNF-α, in which membrane-bound TNF-α but not soluble TNF was shown to activate the TNF type II receptor to cause cell death (Grell et al., Cell, 83, 793–802, 1995) and membrane-bound TNF-α but not soluble TNF is involved in activation of resistance to leishmania (Sypek and Wyler, J.Exp.Med., 174, 755–759, 1991). Recently, Solorzano et al. showed that the metalloproteinase inhibitor BB-2116 potentiates ConA-induced hepatitis in mice (Salorzano et al., J.Immunol., 158, 414–419, 1997). It is possible that the blockage of TNF and FasL shedding in ConA-activated T cells caused the increased cell death of hepatocytes.

When the inventors of the present invention first detected soluble FasL, the inventors thought that it might cause systemic tissue damage, since Fas is expressed in many tissues (Tanaka et al., Nature Med. 2, 317–322, 1996; Tanaka et al., EMBO J., 14, 1129–1135, 1995). However, the finding that the membrane-bound but not soluble FasL has cytotoxic activity suggests that FasL-induced cell death is a local reaction. In immune surveillance, the cytotoxic lymphocytes recognize and are activated by virally infected cells or cancer cells. FasL expressed on the cell surface kills locally the target cells, then is downregulated by shedding. This mechanism may prevent the killing of the healthy bystander cells. Some but not all human patients carrying soluble human FasL in their serum show hepatitis and neutropenia (Tanaka et al., Nature Med. 2, 317–322, 1996), which agrees with the observation that soluble FasL itself is not toxic to normal cells. If the cells are sensitized to Fas-induced apoptosis, for example, by upregulating Fas expression, then they will be killed by soluble FasL.

FasL is constitutively expressed in the eye and testis, and thus its role in immune evasion has been suggested (Bellgrau et al., Nature 377, 630–632, 1995; Griffith et al., Science, 270, 1189–1192, 1995). Applying this phenomenon, several groups have recently tried to express FasL with the transplants to avoid immune attack. In one report, Langerhans β-cells cotransplanted with myoblasts expressing FasL survived longer (Lau et al., Science, 273, 109–112, 1996); in other reports, the β-cells or tumor cells expressing FasL recruited neutrophils and were killed much more quickly than cells that did not express FasL (Allison et al., Proc.Natl.Acad.Sci., 94, 3943–3947, 1997; Seino et al., Nature Medicine, 3, 165–170, 1997). Previously, Karp et al. have reported that tumor cells producing soluble TNF cause inflammation, whereas membrane-associated TNF does not (Karp et al., J.Immunol., 149, 2076–2081, 1992). Thus, it may be interesting to express FasL engineered to produce only the membrane-bound form in transplants.

INDUSTRIAL UTILITY

The present invention provides a soluble Fas ligand which functions as a Fas antagonist, a novel membrane-bound Fas ligand derivative which has excellent cytotoxic activity, and a DNA encoding such peptide, and therefore, the present invention contributes for the treatment and prevention of the disease wherein FasL-induced apoptosis is involved.

What is claimed is:

1. An isolated polypeptide having an amino acid sequence of natural human Fas ligand (SEQ ID NO:17) wherein the 129$^{th}$ amino acid and 130$^{th}$ amino acid residues as measured from N terminal end are both deleted, and at least one amino acid residue from 111$^{th}$ amino acid to 128$^{th}$ amino acid residues or at least one amino acid residue from 131$^{rd}$ amino acid to 133$^{rd}$ amino acid residues as measured from N terminal end is deleted.

2. An isolated polypeptide having an amino acid sequence of natural human Fas ligand (SEQ ID NO:17) wherein all of the 8$^{th}$ amino acid to 69$^{th}$ amino acid residues as measured from N terminal end are deleted, 129$^{th}$ amino acid and 130$^{th}$ amino acid residues as measured from N terminal end are both deleted, and at least one amino acid residue from 111$^{th}$ amino acid to 128$^{th}$ amino acid residues or at least one amino acid residues from 131$^{st}$ amino acid to 133$^{rd}$ amino acid residues as measured from N terminal end is deleted.

3. An isolated polypeptide including the amino acid sequence described in SEQ ID NO:1 or 2.

4. An isolated DNA coding for the polypeptide of claim 1.

5. An isolated DNA coding for the polypeptide of claim 2.

6. An isolated DNA coding for the polypeptide of claim 3.

7. An isolated polypeptide having an amino acid sequence of natural human Fas ligand (SEQ ID NO:17) wherein the 129$^{th}$ amino acid and 130$^{th}$ amino acid residues as measured from N terminal end are both deleted, and at least one amino acid residue from 111$^{th}$ amino acid to 128$^{th}$ amino acid residues or at least one amino acid residue from 131$^{st}$ amino acid to 133$^{rd}$ amino acid residues as measured from N terminal end is deleted, wherein said polypeptide has membrane binding activity and induces Fas-mediated apoptotic activity.

8. An isolated polypeptide having an amino acid sequence of natural human Fas ligand (SEQ ID NO:17) wherein all of the 8$^{th}$ amino acid to 69$^{th}$ amino acid residues as measured from N terminal end are deleted, 129$^{th}$ amino acid and 130$^{th}$ amino acid residues as measured from N terminal end are both deleted, and at least one amino acid residue from 111$^{th}$ amino acid to 128$^{th}$ amino acid residues or at least one amino acid residues from 131$^{st}$ amino acid to 133$^{rd}$ amino acid residues as measured from N terminal end is deleted, wherein said polypeptide has membrane binding activity and induces Fas-mediated apoptotic activity.

9. An isolated peptide having an amino acid sequence of natural human Fas ligand (SEQ ID NO:17) wherein at least four amino acid residues, including 128$^{th}$ and 131$^{st}$ amino acid residues are continuously deleted from the 111$^{th}$ amino acid to the 133$^{rd}$ amino acid residues as measured from N terminal end.

* * * * *

UNITED STATES PATENT AND TRADEMARK OFFICE
CERTIFICATE OF CORRECTION

PATENT NO. : 6,951,919 B1 Page 1 of 1
DATED : October 4, 2005
INVENTOR(S) : Shigekazu Nagata et al.

It is certified that error appears in the above-identified patent and that said Letters Patent is hereby corrected as shown below:

<u>Title page,</u>
Item [75], Inventors, should read -- Shigekazu Nagata, Osaka (JP); Masato Tanaka, Osaka (JP) --.

Signed and Sealed this

Second Day of May, 2006

JON W. DUDAS
*Director of the United States Patent and Trademark Office*

UNITED STATES PATENT AND TRADEMARK OFFICE
CERTIFICATE OF CORRECTION

PATENT NO. : 6,951,919 B1 Page 1 of 1
APPLICATION NO. : 09/508849
DATED : October 4, 2005
INVENTOR(S) : Shigekazu Nagata et al.

It is certified that error appears in the above-identified patent and that said Letters Patent is hereby corrected as shown below:

Title page, item [75]
The inventor should read as follows:

Inventors: Shigekazu Nagata, Osaka (JP); Masato Tanaka, Osaka (JP)

Title Page
The Assignees should read as follows:

(73) Assignee: Mochida Pharmaceutical Co., Ltd., Tokyo (JP); Osaka Bioscience Institute, Osaka (JP)

Signed and Sealed this

Twenty-fourth Day of April, 2007

JON W. DUDAS
*Director of the United States Patent and Trademark Office*